United States Patent [19]
Kato

[11] Patent Number: 5,439,131
[45] Date of Patent: Aug. 8, 1995

[54] ASSEMBLY INCLUDING CONTAINER, CLOSURE AND OPERATING MEANS

[75] Inventor: Takao Kato, Fujieda, Japan

[73] Assignee: Tokuyama Corporation, Tokuyama, Japan

[21] Appl. No.: 124,639

[22] Filed: Sep. 22, 1993

[30] Foreign Application Priority Data

Sep. 25, 1992 [JP] Japan .................. 4-280846

[51] Int. Cl.$^6$ .............................. B65D 43/76
[52] U.S. Cl. .................. 220/264; 220/326; 220/331
[58] Field of Search ............... 220/264, 326, 334, 335, 220/342, 331, 333, 263; 215/235, DIG. 3; 206/364, 366

[56] References Cited

U.S. PATENT DOCUMENTS

| 2,014,582 | 9/1935 | Putz | 220/264 X |
| 2,016,558 | 10/1935 | Redrup | 220/263 |
| 2,925,190 | 2/1960 | Littleton | 220/263 X |

FOREIGN PATENT DOCUMENTS 63-54296 3/1988 Japan .

Primary Examiner—Jes F. Pascua
Attorney, Agent, or Firm—Beveridge, DeGrandi, Weilacher & Young

[57] ABSTRACT

An assembly that includes a frame, a pair of containers fitted to the frame, a common closure, and an operating assembly for moving the common closure. Each of the pair of containers is constituted by a syringe, and a nozzle portion is formed at the front end of container body of the syringe. The operating assembly includes an operating lever pivotably mounted on the frame, and the common closure is pivotably mounted on the operating lever. The common closure has a pair of cap portions that are fitted to the nozzle portions. When the operating lever is turned in the closing direction up to a predetermined final position, the common closure is moved together with the operating lever, brought to a turning position which is opposed to the nozzle positions, and upon relative rotation of the operating lever with respect to the closure, the closure is further moved toward the nozzle portions. When the operating lever is turned toward the opening direction from the predetermined final position, the common closure moves relative to the operating lever, moved up to the turning position while being separated away from the nozzle portions, and is further moved together with the operating lever.

17 Claims, 5 Drawing Sheets 5,439,131

ASSEMBLY INCLUDING CONTAINER, CLOSURE AND OPERATING MEANS

FIELD OF THE INVENTION

The present invention relates to an assembly which includes a container, a closure and an operating means and is of a form in which the operating means is operated to freely move the closure between a closing position at which a discharge opening of the container is closed and an opening position which is apart from the discharge opening and at which the discharge opening is opened.

DESCRIPTION OF THE PRIOR ART

Japanese Patent Laid-Open Publication No. 54296/1988 (Sho63-54296) discloses an assembly which includes a container with a discharge opening, a closure that is allowed to freely move between a closing position at which the discharge opening of the container is closed and an opening position which is apart from the discharge opening and at which the discharge opening is opened, and an operating means which moves the closure. The container is provided with a support member which is equipped with a closure and an operating member. More specifically, the closure is secured to the tip of a swing arm of which the base end is rotatably mounted on the support member. The operating means includes an operating lever and a connecting lever. One end of the operating lever is pivotably mounted on the support member, the other end of the operating lever is pivotably connected to an end of the connecting lever, and the other end of the connecting lever is pivotably connected to the swing arm.

When the operating lever is turned toward the closing direction, the closure pivots from the opening position to the closing position on the base end of the swing arm, so that the discharge opening of the container is closed by the closure. When the operating lever is turned toward the opening direction, the closure pivots from the closing position to the opening position on the base end of the swing arm, and the discharge opening of the container is opened.

However, the assembly disclosed in the above-mentioned Japanese Patent Laid-Open Publication involves a problem that must be solved as described below. The swing arm to which the closure is secured pivots on a axis which extends substantially vertically to the direction of center axis of the discharge opening of the container, and the closure moves between the closing position and the opening position only by the pivoting motion of the swing arm. Thus, the closure does not move in the direction of center axis of the discharge opening of the container. Therefore, limitation is imposed on the shape of the discharge opening of the container and on the shape of the closure relative to each other; i.e., it is difficult to fully tightly fit the closure to the discharge opening of the container. Because of this reason, the above assembly cannot be adapted to the containers that hold a liquid such as an adhesive liquid, which containers are required the discharge opening to be very hermetically closed.

Further, for example, an adhesive resin cement for dental treatment is widely and practically used in a use in which two kinds of pastes are discharged from different containers and are mixed together as a curable composition. In such a case, it is desired to open the discharge openings of the two containers through simple operation, discharge the pastes in required amounts from the two containers and then, close the discharge openings of the two containers. However, no assembly has yet been proposed that satisfies the above requirements. In designing an assembly that satisfies such requirements, it is also important to reliably and consistently prevent the two kinds of pastes from being mixed together and cured at the discharge openings that is caused by the closures that are improperly fitted to the discharge openings of the two containers.

SUMMARY OF THE INVENTION

The principal object of the present invention, therefore, is to provide an assembly which includes a container, a closure and an operating means and is of a form in which the operating means is operated to freely move the closure between a closing position at which a discharge opening of the container is closed and an opening position at which the closure is apart from the discharge opening and the discharge opening is opened, the closure being so improved as to be moved along a special moving passage so as to be very intimately fitted to the discharge opening of the container.

In addition to achieving the above principal object, another object of the present invention is to provide an assembly in which a single feed closure disposed for the discharge openings of the two containers is caused to move along a predetermined moving passage through a simple operation to open or close the discharge openings of the two containers, while reliably preventing the contents held in the two containers from being mixed at the discharge openings.

According to a first aspect of the present invention, the closure is moved by the operating means in a direction toward the discharge opening of the container in the final stage of the closing passage along which the closure is moved from the opening position to the closing position and in a direction opposite to the discharge opening in the initial stage of the opening passage along which the closure is moved from the closing position to the opening position.

That is, according to the first aspect of the present invention, there is provided an assembly which includes a container with a discharge opening, a closure that is allowed to freely move between a closing position at which said discharge opening of said container is closed and an opening position which is apart from said discharge opening and at which said discharge opening is opened, and an operating means which moves said closure; wherein said operating means includes an operating lever that is mounted being allowed to pivot with respect to said container;

said closure is pivotably mounted on said operating lever; and when said operating lever is turned in a closing direction up to a predetermined final position in order to move said closure from said opening position to said closing position, said closure is brought together with said operating lever to a turning position which is opposed to said discharge opening. The operating lever is turned relative to said closure such that said closure is, moved toward said discharge opening, and is brought to said closing position, and when said operating lever is turned in an opening direction from said predetermined final position in order to move said closure from said closing position to said opening position, said operating lever is turned relative to said closure such that the closure is, brought from said closing position up to said turning position and is then moved together with said operating lever.

In order to achieve the above-mentioned another object according to the second aspect of the present invention, furthermore, a single common closure is disposed for the discharge openings of a pair of containers which are fitted to a frame, and the common closure is moved by the operating means in a direction toward the discharge openings of the containers in the final stage of the closing passage along which the closure moves from the opening position to the closing position and in an opposite direction in the initial stage of the opening passage along which the closure moves from the closing position to the opening position.

That is, according to the second aspect of the present invention, there is provided an assembly which includes a frame, a pair of containers having discharge openings and being mounted on said frame, a common closure that is allowed to freely move between a closing position at which said discharge openings of said containers are closed and an opening position which is apart from said discharge openings of said pair of containers and at which said discharge openings are opened, and an operating means which moves said common closure; wherein said operating means includes an operating lever that is mounted being allowed to pivot with respect to said frame;

said common closure is pivotably mounted on said operating lever; and when said operating lever is turned in a closing direction up to a predetermined final position in order to move said common closure from said opening position to said closing position, said common closure is brought together with said operating lever to a turning position which is opposed to said discharge openings. The operating lever is then turned relative to said closure such that said closure is moved toward said discharge openings, and is brought to said closing position, and when said operating lever is turned in an opening direction from said predetermined final position in order to move said common closure from said closing position to said opening position, said common closure is turned relative to said operating lever, brought from said closing position up to said turning position and is then moved together with said operating lever.

Other objects of the invention and technical advantages brought about by the invention will become apparent from the following description which illustrates in detail preferred embodiments of the present invention with reference to the accompanying drawings.

DETAILED DESCRIPTION OF THE PREFERRED EMBODIMENTS

Figure 1:
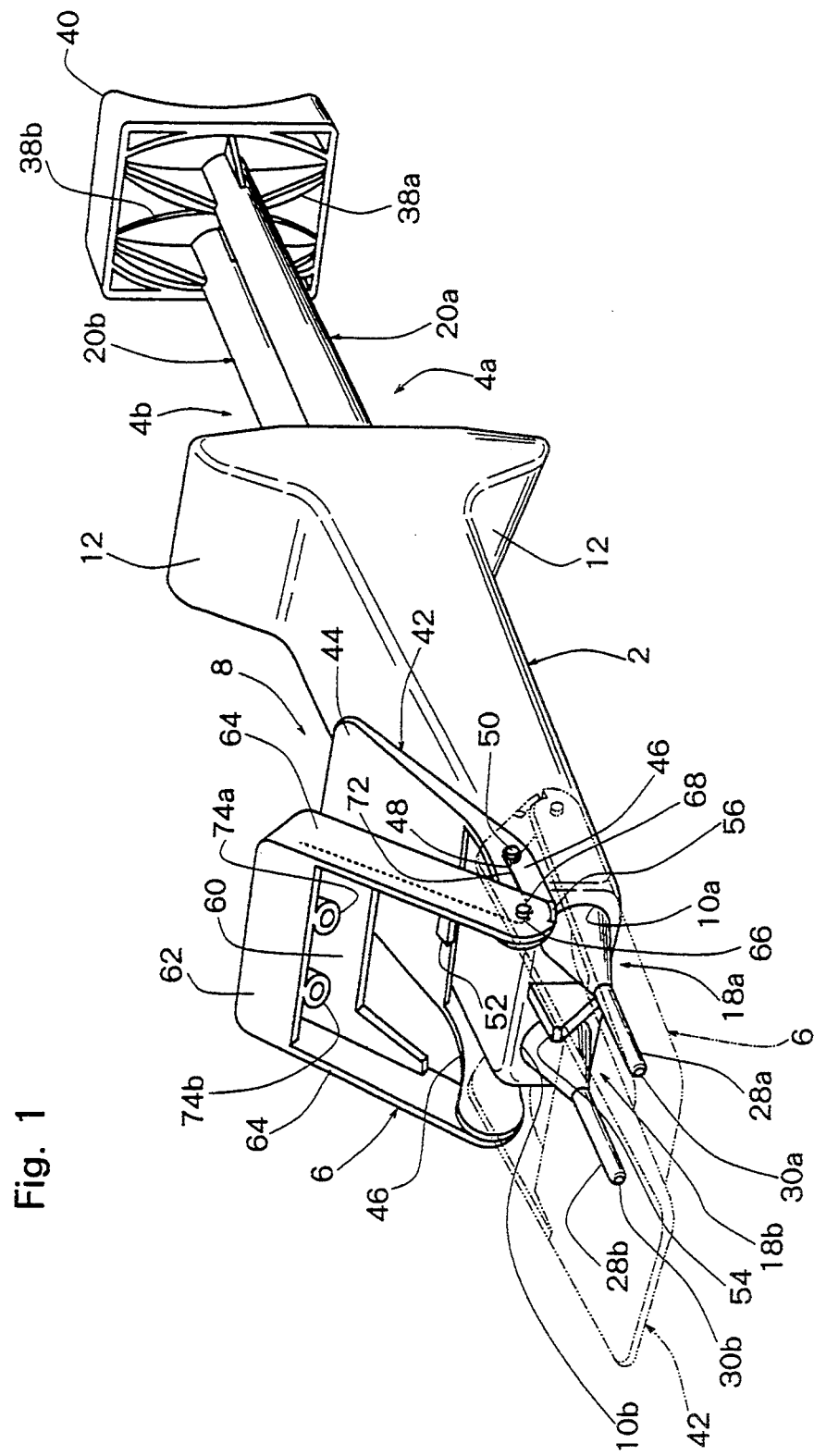
FIG. 1 is a perspective view of an assembly constituted according to a preferred embodiment of the present invention.
Figure 2:
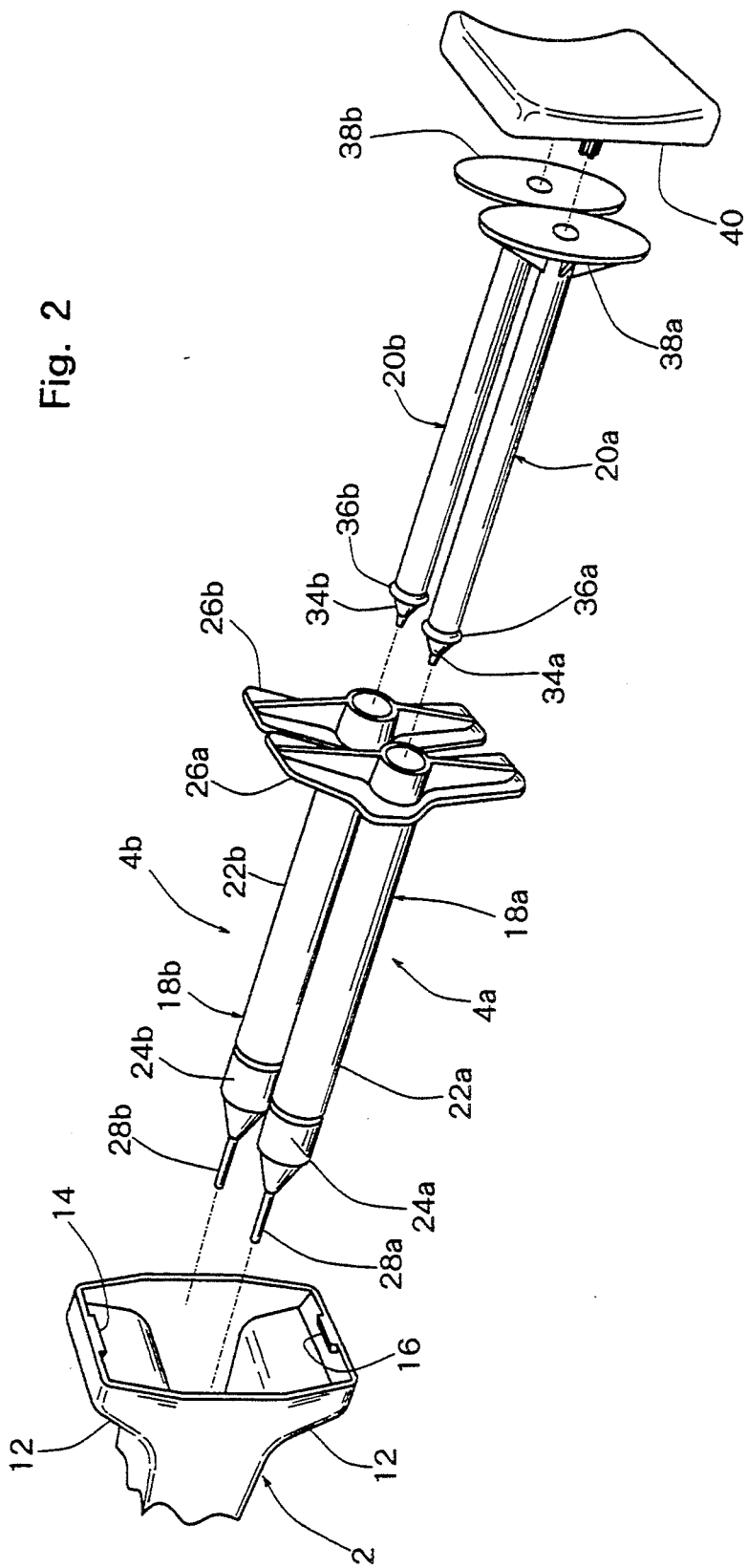
FIG. 2 is a perspective view partially illustrating the assembly of FIG. 1 in a disassembled manner.
Figure 3:
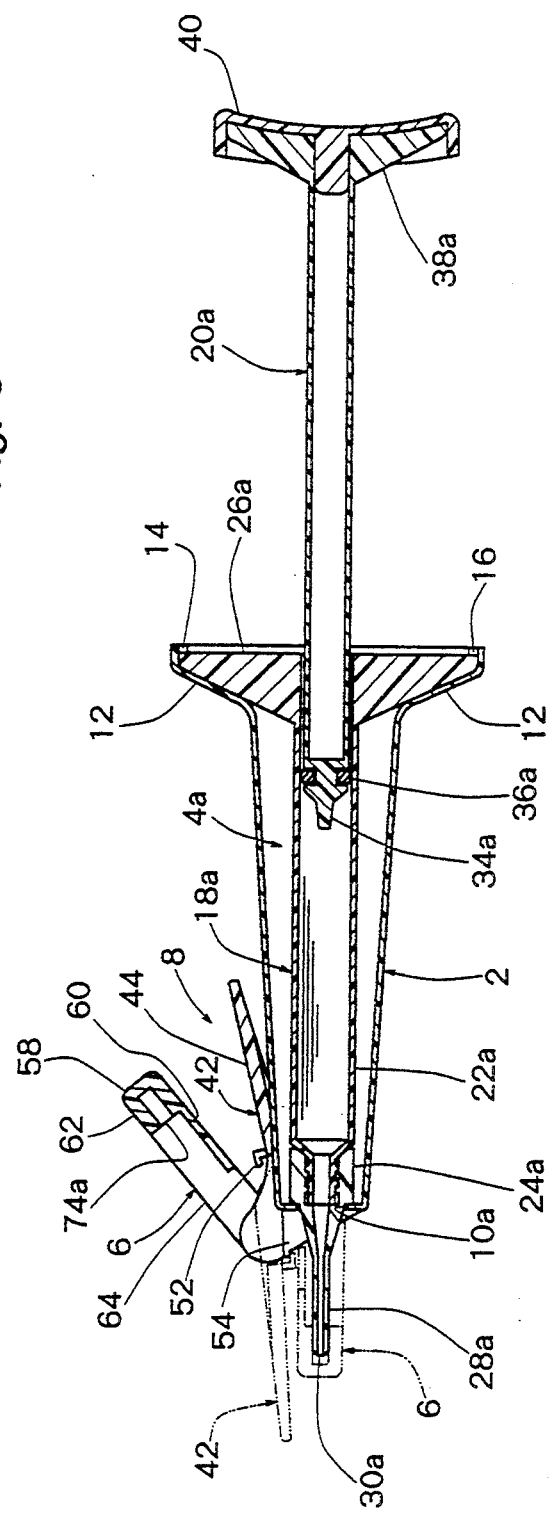
FIG. 3 is a sectional view of the assembly of FIG. 1.

With reference to FIGS. 1 to 3, the illustrated assembly which is constituted according to the present invention includes a frame 2, a pair of containers 4a and 4b, a common closure 6, and an operating means 8.

A main portion of the frame 2 which can be preferably made of a suitable synthetic resin such as polyethylene or polypropylene has the shape of a wedge with its height gradually decreasing toward the front. The frame 2 has two openings 10a and 10b formed in parallel in the front wall thereof. At the rear end of the frame 2, the upper wall and the lower wall extend being respectively steeply tilted upwards and downwards to form a flange portion 12 that protrudes upwards and downwards at the rear end. The rear end surface of the frame 2 is open. As clearly illustrated in FIG. 2, on the rear end surface of the frame 2 are formed an engaging piece 14 that downwardly protrudes from the upper edge thereof and an engaging piece 16 that upwardly protrudes from the lower edge thereof.

With reference to FIGS. 1 to 3, the pair of containers 4a and 4b are constituted by container bodies 18a, 18b and piston members 20a, 20b, respectively. The container bodies 18a and 18b are each constituted by two members, i.e., constituted by first members 22a, 22b and second members 24a, 24b. Main portions of the first members 22a and 22b have a cylindrical shape. As illustrated in FIG. 3, the first members 22a and 22b have at the front ends thereof a circular truncated conical portion of which the diameter gradually decreases toward the front and a small-diameter cylindrical portion which forwardly extends from the circular truncated conical portion. Two annular protuberances are formed at a predetermined distance from each other in the axial direction on the outer peripheral surface of the small-diameter cylindrical portion. The rear end surfaces of the first members 22a and 22b are open. At the rear ends of the first members 22a and 22b are formed protrusions 26a and 26b protruding upwardly and downwardly. The second members 24a and 24b have rear ends of a cylindrical shape and intermediate portions of the shape of a circular truncated cone of which the diameter gradually decreases toward the front, as well as nozzle portions 28a and 28b of the shape of small-diameter cylinders that extend forward from the intermediate portions. Discharge openings 30a and 30b are formed at the front ends of the nozzle portions 28a and 28b. The cylindrical rear ends of the second members 24a and 24b have an inner diameter which corresponds to an outer diameter of the small-diameter cylindrical portions of the first members 22a and 22b, and further have two annular grooves that are formed in the inner peripheral surfaces thereof at a distance in the axial direction. The cylindrical portions of the second members 24a and 24b are fitted onto the small-diameter cylindrical portions of the first members 22a and 22b, and the two annular grooves are brought into resilient engagement with the two annular protuberances in order to couple the second members 24a and 24b to the front ends of the first members 22a and 22b thereby to form the container bodies 18a and 18b. The first members 22a, 22b and the second members 24a, 24b of the container bodies 18a and 18b can be made of any material that does not react with the contents that are held therein. Here, however, it is desired that the first members 22a and 22b are made of a suitable synthetic resin such as polypropylene or polyethylene and that the second members 24a and 24b are made of a relatively soft synthetic resin such as a soft polyethylene. If required, the first members 22a, 22b and the second members 24a, 24b may be made as a unitary structure.

The container bodies 18a and 18b are fitted to the frame 2 in parallel. As clearly illustrated in FIGS. 1 and 3, the container bodies 18a and 18b are inserted in the frame 2 from the rear end surface thereof that is open, and the intermediate portions and the nozzle portions 28a and 28b of the second members 24a and 24b are allowed to protrude forward through the openings 10a and 10b that are formed in the front wall of the frame 2. The protrusions 26a and 26b formed at the rear ends of the container bodies 18a and 18b resiliently get over the engaging pieces 14 and 16 that are formed at the rear end surface of the frame 2, and enter into the rear end of the frame 2. The engaging piece 14 engages with the upper ends of the protrusions 26a and 26b, and the engaging piece 16 engages with the lower ends of the protrusions 26a and 26b, so that the container bodies 18a and 18b are held at the predetermined positions in the frame 2. The container bodies 18a and 18b contain, for example, two kinds of pastes that are used by being mixed together to form an adhesive resin cement for dental treatment.

The containers 4a, 4b and the piston members 20a, 20b can be made of any material that does not react with the contents held in the container bodies 18a and 18b, and should preferably be made of a suitable synthetic resin such as polypropylene or polyethylene. The main portions of the piston members 20a and 20b have a cylindrical shape with a diameter which is slightly smaller than the inner diameter of the main portions of the first members 22a and 22b of the container bodies 18a and 18b. The piston members 20a and 20b have small-diameter shaft portions formed at the front portions thereof as well as front end portions 34a and 34b positioned in front of the small-diameter shaft portions. The front end portions 34a and 34b comprise circular truncated conical portions and small-diameter cylindrical portions that protrude forward beyond the circular truncated conical portions. The small-diameter cylindrical portions have front surfaces which are closed. The small-diameter shaft portions of the piston members 20a and 20b are fitted with seal rings 36a and 36b which are preferably composed of a natural rubber or a synthetic rubber. The seal rings 36a and 36b have an outer diameter which is slightly greater than the inner diameter of the main portions of the container bodies 18a and 18b. When the front ends of the piston members 20a and 20b are inserted in the container bodies 18a and 18b through the rear end surface of the container bodies 18a and 18b as shown in FIGS. 1 and 3, the seal rings 36a and 36b are brought into intimate contact with the inner peripheral surfaces of the container bodies 18a and 18b. Protrusions 38a and 38b are formed at the rear ends of the piston members 20a and 20b protruding upwards and downwards. A single common cover 40 is fitted onto the protrusions 38a and 38b of the piston members 20a and 20b. A pair of protuberances protruding forward are formed on the front surface of the cover 40 that can be made of a suitable synthetic resin material, and are resiliently inserted in the main portions of the piston members 20a and 20b, so that the cover member 40 is coupled to the piston members 20a and 20b. As desired, the cover 40 may be fixed to the protrusions 38a and 38b of the piston members 20a and 20b by a suitable means such as an adhesive agent or the like. Further as desired, the piston members 20a, 20b and the cover member 40 may be constructed as a unitary structure. And further as desired, the cover member 40 is provided with a screw mechanism, and the piston members 20a, 20b are allowed to advance by rotating an input member of the screw mechanism. In the illustrated assembly in which the pair of containers 4a and 4b constituted by the aforementioned syringes are fitted to the frame 2, the front surfaces of the flange portion of the frame 2 are held by the index finger and the middle finger, and the rear surface of the common cover 40 is held by the thumb; i.e., the assembly is held by one hand. Then, the cover 40 is pushed by the thumb to advance the piston members 20a and 20b in the container bodies 18a and 18b, so that the contents in the container bodies 18a and 18b are discharged by required amounts through the discharge openings 30a, 30b of the nozzle portions 28a, 28b.

The description is further continued with reference to FIGS. 1 and 3. The operating means 8 of the illustrated embodiment includes an operating lever 42 which is made of a suitable synthetic resin such as polypropylene or polyethylene. The operating lever 42 has a plate-like grip portion 44 and a pair of arm portions 46 that extend from both sides of the grip portion 44. A hole 48 is formed in each of the pair of arm portions 46. Short shafts 50 are formed at the front ends of both side walls of the frame 2 as a unitary structure, the short shafts 50 protruding in a lateral direction (which is perpendicular to the surface of the paper in FIG. 3) substantially perpendicular to the nozzle portions 28a and 28b. The short shafts 50 of the frame 2 are inserted in the holes 48 of the pair of arm portions 46 of the operating lever 42. Thus, the operating lever 42 is pivotably mounted on the frame 2 to freely pivot between an open limit position indicated by a solid line in FIGS. 1 and 3 and a final closing position indicated by a two-dotted chain line in FIGS. 1 and 3 on the short shafts 50. For inserting the short shafts 50 in the holes 48 of the pair of arm portions 46, the pair of arm portions 46 are resiliently expanded toward a direction to be separated from each other. An L-shaped to-be-engaged piece 52 is formed at a base portion on one surface of grip portion 44 of the operating lever 42. In corresponding to this, an engaging piece 54 is formed at a central portion of front wall of the frame 2. The engaging piece 54 that protrudes forward is of a nearly triangular shape having an upper side which extends nearly horizontally and a lower side which rearwardly extends being tilted downwards. The to-be-engaged piece 52 and the engaging piece 54 constitute in cooperation a lock means which locks the operating lever 42 to the final closing position. In the final stage in which the operating lever 42 is brought to the final closing position from the open limit position, the to-be-engaged piece 52 resiliently gets over the front end of the engaging piece 54 and engages with the lower side of the engaging piece 54, whereby the operating lever 42 is releasably locked at the final closing position. When the operating lever 42 is opened from the final closing position, the to-be-engaged piece 52 resiliently gets over the front end of the engaging piece 54. A sidewardly protruding projection 56 is formed on the outer surfaces at the free ends of the pair of arm portions 46 of the operating lever 42.

With reference to FIGS. 1 and 3, the illustrated assembly has a single common closure 6 that is provided for the pair of containers 4a and 4b. The closure 6 that is made of a suitable synthetic resin such as polypropylene or polyethylene and is constituted as a unitary structure, has a front wall 58, an upper wall 60, a lower wall 62, and a pair of arm portions 64 which extend from both sides of the front wall 58. A hole 66 is formed in each of the pair of arm portions 64. On the other hand, short shafts 68 are formed at the free ends of the pair of arm portions 46 of the operating lever 42, the short shafts 68 protruding in a lateral direction (which is perpendicular to the surface of the paper in FIG. 3) substantially perpendicular to the nozzle portions 28a and 28b. Short shafts 68 of the pair of arm portions 46 of the operating lever 42 are inserted in the holes 66 of the pair of arm portions 64 of the closure 6, so that the closure 6 is pivotably mounted on the operating lever 42. The pivotal axis of the closure 6 (center axis of the short shaft 68) relative to the operating lever 42 and the pivotal axis (center axis of the short shaft 50) of the operating lever 42 relative to the frame 2 (i.e., relative to the containers 4a and 4b) are in parallel with each other, and are substantially perpendicular to the direction in which the nozzle portions 28a and 28b of the containers 4a and 4b extend. With reference to FIGS. 1 and 3 as well as FIGS. 4 to 6, the closure 6 pivots between a first angular position (state indicated by a solid line in FIGS. 1 and 3 and shown in FIGS. 4 and 5) at which an angle $\alpha$ is formed between the closure 6 and the operating lever 42 and a second angular position (state indicated by a two-dotted chain line in FIGS. 1 and 3 and shown in FIG. 6) at which an angle $\beta$ smaller than the angle $\alpha$ is formed therebetween. A notch having a nearly arcuate shape is formed at one free end of the pair of arm portions 64 of the closure to define a contact surface 70. When the closure 6 is brought to the first angular position with respect to the operating lever 42, an end of the projection 56 formed on one of the pair of arms 46 of the operating lever 42 is brought into contact with the contact surface 70 formed in one of the pair of arm portions 64 of the closure 6, and the operating lever 42 is prevented from turning over the first angular position with respect to the operating lever 42. Therefore, the above-mentioned projection 56 and the contact surface 70 constitute in cooperation constitute a turn limit means which limits the turning of the closure 6 to the first angular position with respect to the operating lever 42. As shown in FIG. 1, a resilient urging means constituted by a helical spring 72 is interposed between the operating lever 42 and the closure 6. The helical spring 72 is fitted about the short shaft 68, and its one end is anchored to the short shaft 50 of the operating lever 42, while its other end extends along the inner surfaces of the pair of arm portions 46 of the closure 6 and is anchored to the inner surface of the lower wall 62. The helical spring 72 resiliently urges the closure 6 toward the first angular position with respect to the operating lever 42.

As clearly illustrated in FIGS. 1 and 3, two cylindrical cap portions 74a and 74b are formed between the upper wall 60 and the lower wall 62 of the closure 6 at a distance in the direction of width. The distance between the two cap portions 74a and 74b corresponds to the distance between the nozzle portions 28a and 28b of the pair of containers 4a and 4b, and the inner diameter of the cap portions 74a and 74b corresponds to the outer diameter of the nozzle portions 28a and 28b. As clearly shown in FIG. 1, the rear edge of the lower wall 62 is in match with the rear edges of the cap portions 74a and 74b, but the upper wall 60 rearwardly extends beyond the rear edges of the caps 74a and 74b.

Figure 4:
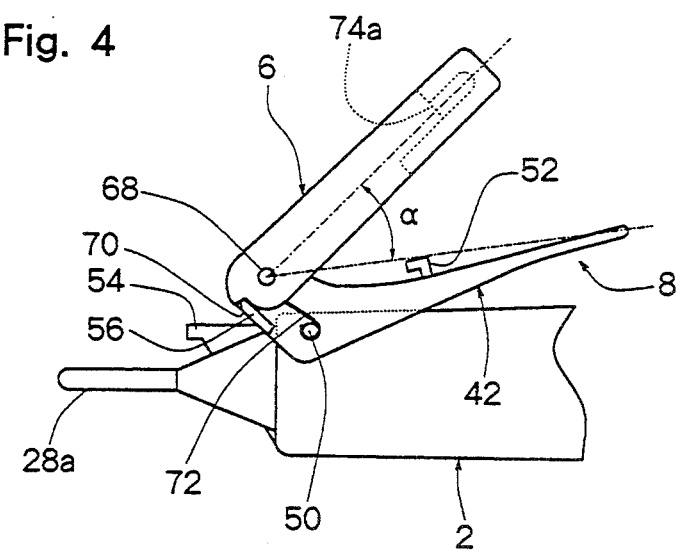
FIGS. 4 to 6 are partial side views illustrating the manner of motion of an operating means and a closure of the assembly of FIG. 1.
Figure 5:
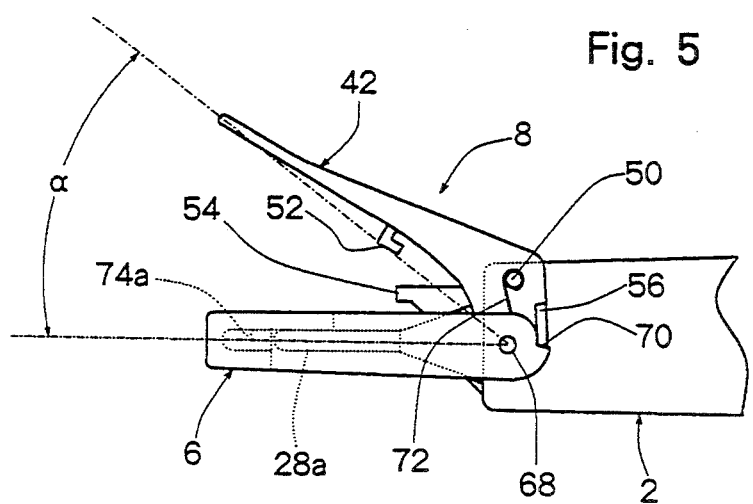

Under the state indicated by a solid line in FIGS. 1 and 3 and shown in FIG. 4, the closure 6 is located at the opening position, and the cap portions 74a and 74b are apart from the nozzle portions 28a and 28b of the containers 4a and Therefore, the discharge openings 30a and 30b formed at the ends of the nozzle portions 28a and 28b are opened. When the operating lever 42 is turned in the counterclockwise direction in FIGS. 4 and 5 on the short shafts 50 by gripping the grip portion 44 of the operating lever 42, the closure 6 also pivots with the turning of the operating lever 42 on the short shafts 50 until the state shown in FIG. 5 is reached. Under the state shown in FIG. 5, the closure 6 is located at a turning position. At the turning position, the inner surface of the upper wall 60 of the closure 6 comes in contact with the nozzle portions 28a and 28b of the containers 4a and 4b, and consequently, the closure 6 is prevented from turning in the counterclockwise direction in FIG. 5 over the turning position. Accordingly, the rear extending portion of the upper wall 60 constitutes a turning position pass-blocking means which blocks the closure 6 from getting over the turning position. The second members 24a, 24b having the nozzle portions 28a, 28b are made of a relatively soft synthetic resin as described above. Hence, there is no risk of the nozzle portions 28a, 28b being damaged by the contact with the upper wall 60 of the closure 6. When the closure 6 is located at the turning position as is obvious from FIG. 5, the cap portions 74a and 74b of the closure 6 are positioned in match with the axial direction of the nozzle portions 28a and 28b of the containers 4a and 4b, and are hence positioned being opposed to the discharge openings 30a and 30b of the nozzle portions 28a and 28b. When the operating lever 42 is further turned in the counterclockwise direction in FIGS. 5 and 6, the closure 6, which is prevented from further turning in the counterclockwise direction, is rightwardly moved in the axial direction of the nozzle portions 28a and 28b in FIGS. 5 and 6 while short shafts 68 rotate within arm holes 66. When the operating lever 42 is turned up to the final closing position shown in FIG. 6, the closure 6 is moved up to the closing position shown in FIG. 6, whereby the cap portions 74a and 74b of the closure 6 are sufficiently capped to the nozzle portions 28a and 28b of the containers 4a and 4b, and the discharge openings 30a and 30b of the nozzle portions 28a and 28b are closed. As the operating lever 42 is brought to the final closing position shown in FIG. 6, the to-be-engaged piece 52 of the operating lever 42 works to lock the operating lever 42 in cooperation with the engaging piece 54 formed on the frame 2. The closure 6 is thus locked at the closing position.

Figure 6:
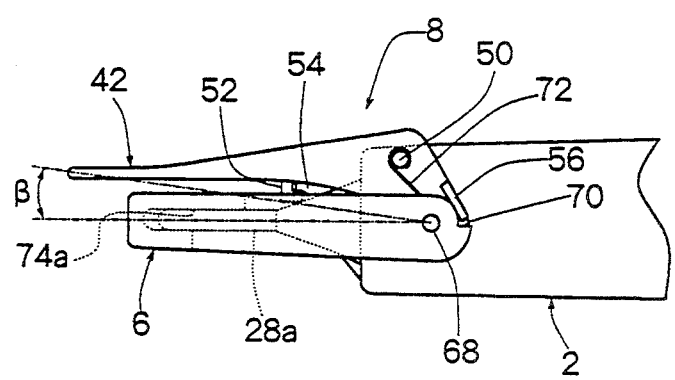

In order to open the discharge openings 30a and 30b of the nozzle portions 28a and 28b, the grip portion 44 of the operating lever 42 is gripped to turn the operating lever 42 in the clockwise direction in FIGS. 6 and 5 on the short shafts 50. When the operating lever 42 is turned from the final closing position shown in FIG. 6 to a position shown in FIG. 5, the closure 6 is caused to pivot with respect to the operating lever 42 on the short shafts 68 and is brought to the second angular position and is leftwardly moved in the axial direction of the nozzle portions 28a and 28b in FIGS. 6 and 5 so as to be brought to the turning position shown in FIG. 5. At the turning position, the caps 74a and 74b of the closure 6 are separated away from the nozzle portions 28a and 28b. When the operating lever 42 is clockwisely turned in FIGS. 5 and 4 from the state shown in FIG. 5 to the state shown in FIG. 4, the closure 6 pivots in the clockwise direction with the turning of the operating lever 42 up to the opening position shown in FIG. 4 on the short shafts 50. Thus, the closure 6 is sufficiently separated away from the nozzle portions 28a and 28b, and the contents in the containers 4a and 4b are allowed to be discharged through the discharge openings 30a and 30b of the nozzle portions 28a and 28b.

Figure 7:
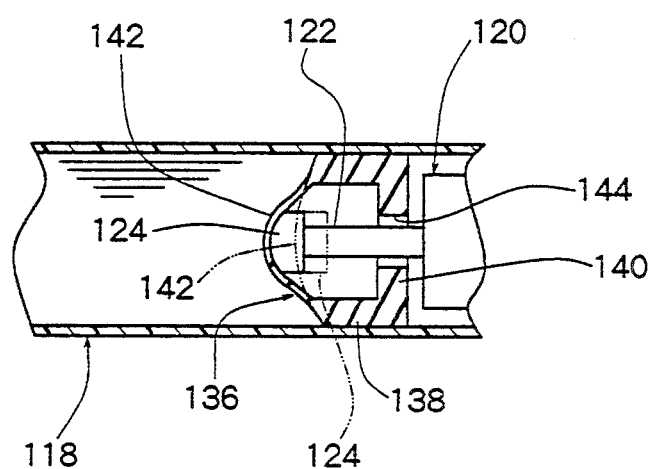
FIG. 7 is a partial sectional view illustrating a modified syringe in the assembly of FIG. 1.

FIG. 7 illustrates a modified example of the piston member in the container. At the front end of the piston member 120 shown in FIG. 7 is formed a small-diameter cylindrical portion 122 that protrudes forward and a push block 124 located at the front end thereof. The front surface of the push block 124 is smoothly curved. A sealing member 136 is fitted to the small-diameter cylindrical portion 122 and to the push block 124. The sealing member 136 which should preferably be made of an elastic material having excellent softness such as a natural rubber or a synthetic rubber, has a side sealing wall 138 of a cylindrical shape, a rear wall 140 and a front wall 142. An opening 144 is formed at the center of the rear wall 140, and the small-diameter cylindrical portion 122 and the push block 124 protrude forward through the opening 144. The front wall 142 is relatively thin. The side sealing wall 138 of the sealing member 136 has an outer diameter which is slightly greater than the inner diameter of the main portion of the container body 118, and is brought into contact with the inner peripheral surface of the main portion of the container body 118. When an operator moves the piston member 120 forward (leftwards in FIG. 7) to discharge the content in the container body 118, the push block 124 acts on the front wall 142 of the sealing member 136 as indicated by a solid line in FIG. 7 whereby the front wall 142 elastically swells forward and the sealing member 136 moves forward with the movement of the piston member 120. When the operator removes his hand from the piston member 120 after the discharge operation of the content has been finished, the front wall 142 of the sealing member 136 elastically restores to the initial flat state from the swollen state as indicated by a two-dotted chain line in FIG. 7, and the piston member 120 slightly moves back. A negative pressure is produced to a slight degree in the container body 118 due to the restoration of the front wall 142 of the sealing member 136, whereby the content is slightly sucked into the inside from the discharge opening of the container body 118 and the content is very reliably prevented from leaking out of the discharge opening.

In the foregoing it was described in detail a preferred embodiment of the assembly constituted according to the present invention with reference to the accompanying drawings. It should, however, be noted that the invention is in no way limited to the above embodiment only but can be varied or modified in a variety of other ways without departing from the scope of the invention.

In the above-mentioned embodiment, for instance, a pair of containers are fitted to the frame, and a single common closure and a single operating means are disposed for the pair of containers. As required, however, one closure and one operating means may be disposed independently for each container. Moreover, the operating means and the closure may be directly mounted on the container without using a frame. In the aforementioned embodiment, the containers are constituted by syringes. The present invention, however, can be adapted to even such containers as bottles made of a glass, a thin metal plate and a synthetic resin, as well as tube containers.

In the above-mentioned embodiment, the upper wall of the closure is brought in contact with the nozzle portions of the containers to prevent the closure from turning over the turning position. It is, however, also allowable to provide the frame or the containers with a contact piece which, when the closure is turned to the turning position, comes in contact with the arm or other portion of the closure to prevent the closure from turning any more. In the above embodiment, furthermore, the cap portions that fit to the nozzle portions of the container are formed in the closure. It is, however, also allowable to provide the closure with a closing means of any other form such as plugs that can be inserted in the discharge openings of the nozzle portions instead of the cap portions.

What I claim is:

1. An assembly which includes:
   a container with a discharge opening;
   a closure that is moveable between a closing position at which said discharge opening of said container is closed and an opening position which is apart from said discharge opening and at which said discharge opening is opened;
   an operating assembly which includes an operating lever that is pivotable with respect to said container on a mount that is fixed in position relative to said container;
   said closure being pivotably mounted on said operating lever; and a pivotal axis of said operating lever relative to said container and a pivotal axis of said closure relative to said operating lever are substantially in parallel with each other; and a center axis of said discharge opening extends substantially perpendicularly to the pivotal axis of said operating lever relative to said container and substantially perpendicularly to the pivotal axis of said closure relative to said operating lever;
   said operating assembly and said closure being dimensioned and arrange with respect to said container such that, when said operating lever is moved in a closing direction to a predetermined final position in order to move said closure from said opening position to said closing position, said closure is brought together with said operating lever to a turning position which is opposed to said discharge opening and which features said operating lever being at a first angular position with respect to said closure, and upon a modification in the relative position of said operating lever and closure wherein the first angular position is changed to a second angular position, said closure is moved substantially in the direction of the center axis of said discharge opening from said turning position to said closing position, and when said operating lever is turned in an opening direction from said predetermined final position in order to move said closure from said closing position to said opening position, said closure is brought from said closing position to said turning position and is then moved together with said operating lever.

2. An assembly according to claim 1, wherein said operating lever freely pivots between the first angular position at which an angle α is formed between said closure and said operating lever and the second angular position at which an angle β, smaller than said angle α, is formed between said closure and said operating lever, and during the pivoting of said operating lever from said first angular position to said second angular position, said closure is moved substantially in the direction of the center axis of said discharge opening.

3. An assembly according to claim 2, wherein
a resilient urging means is provided between said operating lever and said closure to resiliently urge said closure toward said first angular position relative to said operating lever; and
a turn limit means is provided on said closure to prevent said closure from turning over said first angular position relative to said operating lever.

4. An assembly according to claim 1, wherein said closure includes a turn position pass-blocking means which prevents said closure from moving together with said operating lever over said turning position at the time when said operating lever is brought from said first angular position to said second angular position.

5. An assembly according to claim 4 wherein said turn position pass-blocking means includes an upper wall, and said first and second pivot axis are spaced apart and said upper wall is dimensioned and arranged such that said upper wall contacts said container when said closure is in said turning position.

6. An assembly according to claim 1, wherein said operating assembly includes locking means which releasably locks said operating lever at said predetermined final position.

7. An assembly according to claim 1, wherein
said container is a syringe which includes a container body having a cylindrical holding portion of which a front end constitutes a nozzle portion and of which a base end is open, and a piston member which is inserted in said cylindrical holding portion through said base end, said discharge opening being formed at the front end of said nozzle portion; and
on the front end of said piston member is mounted a sealing member made of an elastic material having a front wall and a side sealing wall that comes in intimate contact with an inner peripheral surface of said cylindrical holding portion and, when said piston member is forwarded in said cylindrical holding portion, the front end of said piston member acts on said front wall of said sealing member so that said front wall is elastically swollen forward.

8. An assembly according to claim 1 wherein said mount is a component of said container such that said operating assembly is directly mounted on said container.

9. An assembly, according to claim 1 further comprising a frame structure supporting said container and wherein said mount is a component of said frame structure on which said container is mounted.

10. An assembly, comprising:
a frame;
a pair of containers mounted on said frame, said containers including discharge openings;
an operating assembly which includes an operating lever pivotably mounted on said frame about a first pivot axis;
a common closure that is pivotably mounted on said operating lever about a second pivot axis which is parallel with said first pivot axis, and said common closure being moveable between a closing position at which said discharge openings of said containers are closed and an opening position which places said common closure apart from said discharge openings such that said discharge openings are opened;
and said operating assembly and common closure being dimensioned and arranged with respect to said containers such that when said operating lever is turned in a closing direction up to a final closing position in order to move said common closure from said opening position to said closing position, said common closure is brought together with said operating lever to a turning position which places said common closure opposed to said discharge openings and has said operating lever in a first angular position with respect to said closure, and, upon said operating lever being adjusted with respect to said common closure to a second angular position, said common closure is moved toward said discharge openings and is brought to said closing position, and when said operating lever is turned in an opening direction from said final position in order to move said common closure from said closing position to said opening position, said operating lever is turned relative to said common closure such that said common closure is brought from said closing position to said turning position and is then moved together with said operating lever.

11. An assembly according to claim 10, wherein
each of said pair of containers is a syringe which includes a container body having a cylindrical holding portion of which a front end constitutes a nozzle portion and of which a base end is open, and a piston member which is inserted in said cylindrical holding portion through said base end, said pair of syringes extending in parallel with each other, the nozzle portions of said pair of syringes protruding beyond the front end of said frame, and said discharge openings being formed at the front ends of said nozzle portions;
said common closure has a pair of cap portions that are fitted to said nozzle portions of said pair of syringes;
said operating lever is pivotably mounted on the front end of said frame;
said pair of syringes extend substantially perpendicularly to the pivotal axis of said operating lever relative to said frame and substantially perpendicularly to the pivotal axis of said common closure relative to said operating lever; and
said common closure is moved substantially in the axial direction of said pair of syringes upon movement of said operating lever from said first angular position to said second angular position during closing of said discharge openings and upon movement of said operating lever from said second angular position to said first angular position during opening of said discharge openings.

12. An assembly according to claim 11, wherein on the front end of said piston member of each of said pair of syringes there is mounted a sealing member made of an elastic material having a front wall and a side sealing wall that comes in intimate contact with the inner peripheral surface of said cylindrical holding portion and, when said piston member is forwarded through said cylindrical holding portion, the front end of said piston member acts on said front wall of said sealing member so that said front wall is elastically swollen forward.

13. An assembly according to claim 11, wherein the container bodies of said pair of syringes hold two kinds of pastes that are mixed together to form an adhesive resin cement for dental treatments.

14. An assembly according to claim 10, wherein
said common closure is allowed to freely pivot between the first angular position at which an angle $\alpha$ is formed between said closure and said operating lever and the second angular position at which an angle $\beta$, which is smaller than said angle $\alpha$, is formed between said closure and said operating lever.

15. An assembly according to claim 14, wherein
a rotation limit means is provided on said common closure to prevent said common closure from turning over said first angular position relative to said operating lever; and
a resilient urging means is provided between said operating lever and said common closure to resiliently urge said common closure toward said first angular position relative to said operating lever.

16. An assembly according to claim 10, wherein said common closure is provided with a turn position pass-blocking means which prevents said common closure from moving together with said operating lever over said turning position upon said common closure coming in contact with said nozzle portions of said pair of syringes at the time when said operating lever is turned in the closing direction to move said common closure from said opening position to said closing position.

17. An assembly according to claim 10, further comprising
locking means which releasably locks said operating lever at said predetermined final position; and
said locking means is constituted by an engaging projection formed on said frame and a projection that is to be engaged, formed on said operating lever, and said projection to be engaged resiliently passes over said engaging projection when said operating lever is turned to said predetermined final position.

* * * * *